United States Patent [19]

Asahina

[11] Patent Number: 5,125,018
[45] Date of Patent: Jun. 23, 1992

[54] X-RAY DIAGNOSTIC APPARATUS
[75] Inventor: Hiroshi Asahina, Nishinasuno, Japan
[73] Assignee: Kabushiki Kaisha Toshiba, Kawasaki, Japan
[21] Appl. No.: 723,329
[22] Filed: Jun. 28, 1991
[30] Foreign Application Priority Data
  Jun. 29, 1990 [JP] Japan .................. 2-173286
[51] Int. Cl.$^5$ .............................. H05G 1/64
[52] U.S. Cl. ..................... 378/99; 378/108
[58] Field of Search ............ 378/99, 108; 358/111
[56] References Cited

U.S. PATENT DOCUMENTS

4,477,923 10/1984 Baumann et al. ............ 378/99
4,626,908 12/1986 Tani ............................. 378/99
4,703,496 10/1987 Meccariello ................. 378/108

Primary Examiner—Craig E. Church
Attorney, Agent, or Firm—Oblon, Spivak, McClelland, Maier & Neustadt

[57] ABSTRACT

An X-ray diagnostic apparatus including an imaging system in which X-rays are applied to a subject and a picture image in response to an X-ray does transmitted through the subject is displayed comprises an X-ray generator for generating an X-ray a detecting unit for detecting the X-ray generated from the X-ray generator and passing through the subject disposed between the X-ray generator and the detecting unit and for generating a signal in response to the detected X-ray, a deciding unit operatively connected to the detecting unit for deciding an optimum imaging condition for a portion of the subject to be imaged before a start of an imaging process, a unit for detecting whether the imaging system or the subject is being moved or not, and a controlling unit for controlling the imaging condition within a predetermined interval of time during or after the movement of the imaging system or the subject. The detecting unit for the movement of the imaging system or the subject includes a first recording memory for recording the digital signal just before injecting a contrast medium successively as a mask image, a second recording memory for recording the digital signal after injecting the contrast medium successively as a transmitted image.

4 Claims, 6 Drawing Sheets

X-RAY DIAGNOSTIC APPARATUS

BACKGROUND OF THE INVENTION

The present invention relates to an X-ray diagnostic apparatus wherein X-rays are applied to a subject, and a picture according to a transmitted X-ray dose is displayed on a monitor.

When imaging or photographing a desired portion of a subject, such as a living human body, i.e. patient, on an X-ray diagnostic apparatus, the prevailing method is such that the desired portion is image photographed continuously for a certain period of time as in the case of cinemato-graphing. The cinematographing is intended for observation of a contrast image, and an X-ray imaging or photographing system (hereinafter simply called imaging system) or the subject may be moved regardless of imaging process. For keeping a cinefilm density constant in this case, an outgoing light of I. I. (image intensifier) for inputting X-rays having passed through the subject is detected by a photoelectron multiplier and a detected result is fed back to a high voltage generator, thereby controlling X-ray imaging or photographing conditions (hereinafter simply called imaging conditions) such as tube voltage, tube current and the like. Further, the outgoing light of I. I. also changes when a visual field mode of I. I. is changed, therefore the imaging conditions are controlled according to a similar method.

On the other hand, DSA (Digital Subtraction Angiography) is employed as another imaging system on the X-ray diagnostic apparatus for the purpose of subtraction between picture images. To move the imaging system or subject during imaging process in the DSA as in the case of aforementioned cinematographing is to lead to an erroneous subtraction, thus an artifact may arise on a DSA image (subtraction image) to bring about a picture image improper to diagnosis. Further, to change the imaging conditions during imaging process is also to cause a change in density of the DSA image, and a diagnostic efficiency may deteriorate, which is not preferable. Accordingly, in the DSA optimum imaging conditions will be decided immediately before the start in the imaging process, which is then carried out with the imaging conditions being fixed thereto.

In recent years, meanwhile, a non-ionic contrast medium has been developed, and a dosage is less limited, therefore a contrast examination with the object of observing a contrast image in view without subtraction has increased also in DSA examination carried out on a digital image processing unit. As in the case of aforementioned cinematographing, a movement of the imaging system or subject and imaging conditions during the imaging process may be controlled. In case the imaging system and the subject are fixed while an observation of the contrast image is a principal object, there is a demand for utilizing the DSA image subjected to a subtraction process as diagnosis information under the state where the artifact and the change in density caused thereon are not to deteriorate severely a diagnostic efficiency.

Meanwhile, according to the prior art technology described above, there is a problem inherent in a prior art X-ray diagnostic apparatus such that if the imaging conditions are controlled whenever the DSA is carried out as mentioned, an outgoing light of I. I. changes according to an inflow of the contrast medium and thus the imaging conditions are changed. Besides, if the imaging conditions are fixed, the outgoing light of I. I. becomes excessively high or low in accordance with a movement of the imaging system or subject, therefore a density of the contrast image comes to change largely.

SUMMARY OF THE INVENTION

An object of the present invention is to substantially eliminate defects or drawbacks encountered in the prior art and to provide an X-ray diagnostic apparatus capable of obtaining the DSA image after movement of the imaging system or subject in an optimized condition in addition to a diagnosis securable by observation of a contrast image.

Another object of the present invention is to provide an X-ray diagnostic apparatus including a recording memory for recording an X-ray image when the X-ray imaing conditions are optimized after the stopping of the movement of the imaging system or the subject.

These and other objects can be achieved according to the present invention by providing an X-ray diagnostic apparatus including an imaging system in which X-rays are applied to a subject to be imaged and a picture image in response to an X-ray dose transmitted through the subject is displayed, the apparatus comprising an X-ray generator for generating an X-ray a detecting unit for detecting the X-ray generated from the X-ray generator and passing through the subject disposed between the X-ray generator and the detecting unit and for generating a signal in response to the detected X-ray, a deciding unit operatively connected to the detecting unit for deciding an optimum imaging condition for a portion of the subject to be imaged before a start of an imaging process, a unit for detecting whether the imaging system or the subject is being moved or not, a controlling unit for controlling the imaging condition within a predetermined interval of time during or after the movement of the imaging system or the subject, and a display unit connected to the optimum condition deciding unit.

In a preferred embodiment, the imaging condition deciding unit includes signal input units for inputting signals from the X-ray detecting unit and the imaging system and subject movement detecting unit, an optimum imaging condition setter operatively connected to the signal input unit and an imaging condition decider and the controlling units includes a high voltage generator operatively connected to the optimum imaging condition setter and the X-ray generator.

The detecting unit for detecting the movement of the imaging system or the subject comprises a digital fluorography device including an analog-to-digital converter for converting a signal from the X-ray detecting unit to a digital signal, a signal input unit operatively connected to the controlling unit, a first recording memory for recording the digital signal just before injecting a contrast medium successively as a mask image, a second recording memory for recording the digital signal after injecting the contrast medium successively as a transmitted image, and a subtraction processor for subtracing the transmitted image from the mask image. The subtraction processor is operatively connected to the display unit through a digital-to-analog convertor.

According to the X-ray diagnostic apparatus of the characters described above, a position of the imaging system or the subject is detected and while these are in the fixed states, the imaging conditions are fixed the imaging conditions are controlled within a given period of time while the imaging system or the subject is moved and after the movement stops. Thus, a picture imaged when the imaging system or the subject is fixed can effectively be put to practical use for subtraction process. Where the imaging system or the subject are moved thereafter, the optimum imaging conditions can be set according to a change of the subject. A density of the contrast image can be optimized and the DSA image free from a change in density is obtainable consequently, and further the DSA image not shifted at a position after the imaging system or the subject is moved is obtainable.

BRIEF DESCRIPTION OF THE DRAWINGS

For a better understanding of the present invention and to show how the same is carried out, reference is first made, by way of preferred embodiment, to the accompanying drawings; in which.

DESCRIPTION OF THE PREFERRED EMBODIMENTS

Figure 1:
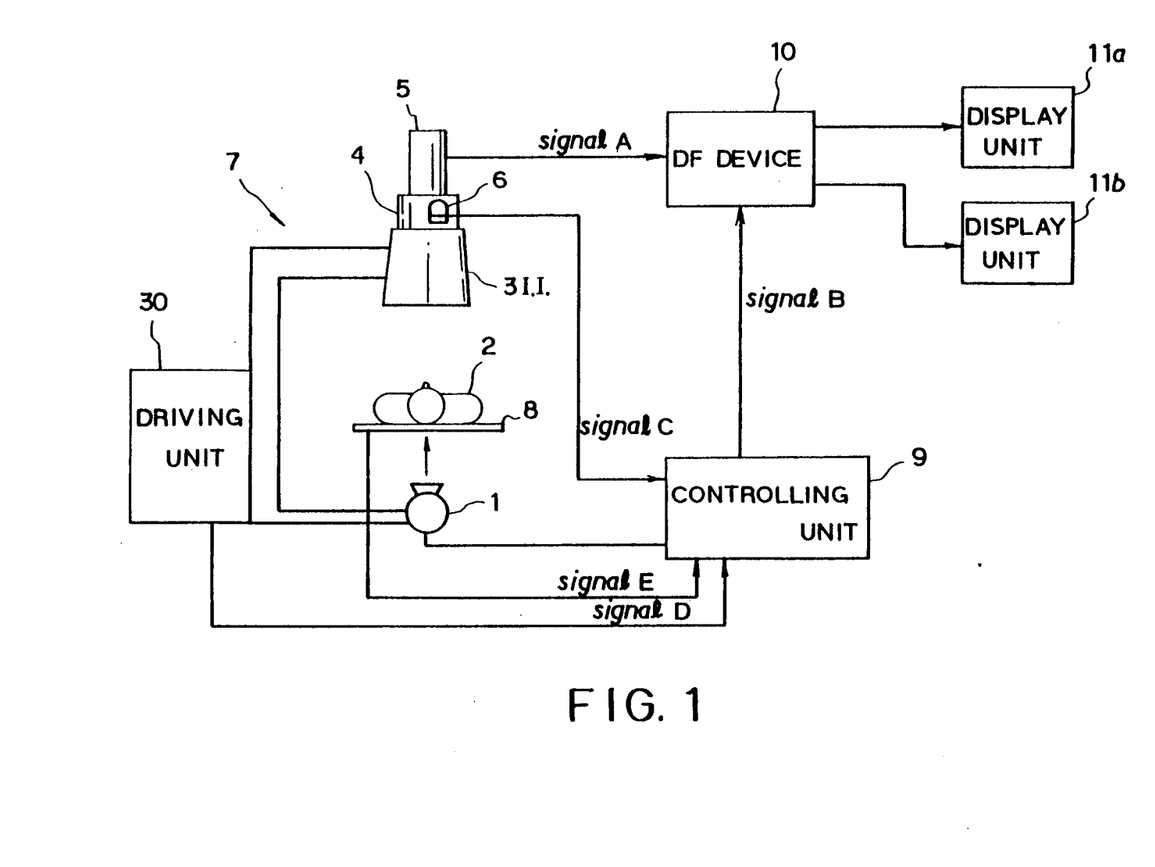
FIG. 1 is a block diagram representing an X-ray diagnostic apparatus of one preferred embodiment of the present invention.

FIG. 1 is a block diagram representing an X-ray diagnostic apparatus of one embodiment of the present invention, wherein a reference numeral 1 denotes an X-ray tube for generating the X-rays for irradiating a subject 2, i.e. patient, supported on a bed 8. An I. I. (image intensifier) 3 to which X-rays having passed through the subject are inputted is disposed above the bed 8 and an optical unit 4 is mounted to the I.I. 3. A TV camera 5 for imaging an optical image on the I. I. 3 is connected to the optical unit 4 and a photoelectron multiplier 6 for detecting a part of an outgoing light of the I. I. 3 is connected to the I.I. 3. The imaging system is supported by an imaging system support 7. The X-ray diagnosis apparatus further includes a controlling unit 9 including a high voltage generator, a DF (digital fluorography) device 10 and TV monitors 11a and 11b, which will be described in detail hereinlater. A reference numeral 30 denotes a driving means for driving the imaging system.

The X-ray tube 1, the I. I. 3, the optical system 4, and the TV camera 5 construct an imaging system and are supported on the imaging system support 7. The X-ray tube 1 irradiates X-rays by a high voltage supplied from the high voltage generator in the controlling unit 9, the X-rays having passed through the subject 2, i.e. patient laid on the bed 8, are transformed into a light by the I. I. 3, which passes through the optical system 4 to be incident on the TV camera 5 and transformed into a video signal. A part of optical information is transformed into an electrical signal C by the photoelectron multiplier 6 when passing through the optical system 4, and is inputted to the controlling unit 9 as a controlling signal.

The video signal (signal A) outputted from the TV camera 5 is inputted to the DF device 10 for an image processing operation, then a transmitted image is displayed on the TV monitor 11a, and a DSA image is displayed on the TV monitor 11b. When the imaging system is moving, a signal D indicating the movement is inputted to the high voltage generator of the controlling unit 9. Then, when the bed 8 is moving, that is, the subject 2 is moving, a signal E indicating the movement is inputted to the controlling unit 9. Further, a signal B indicating that imaging conditions are decided is inputted to the DF device 10 from the controlling unit 9.

Figure 2:
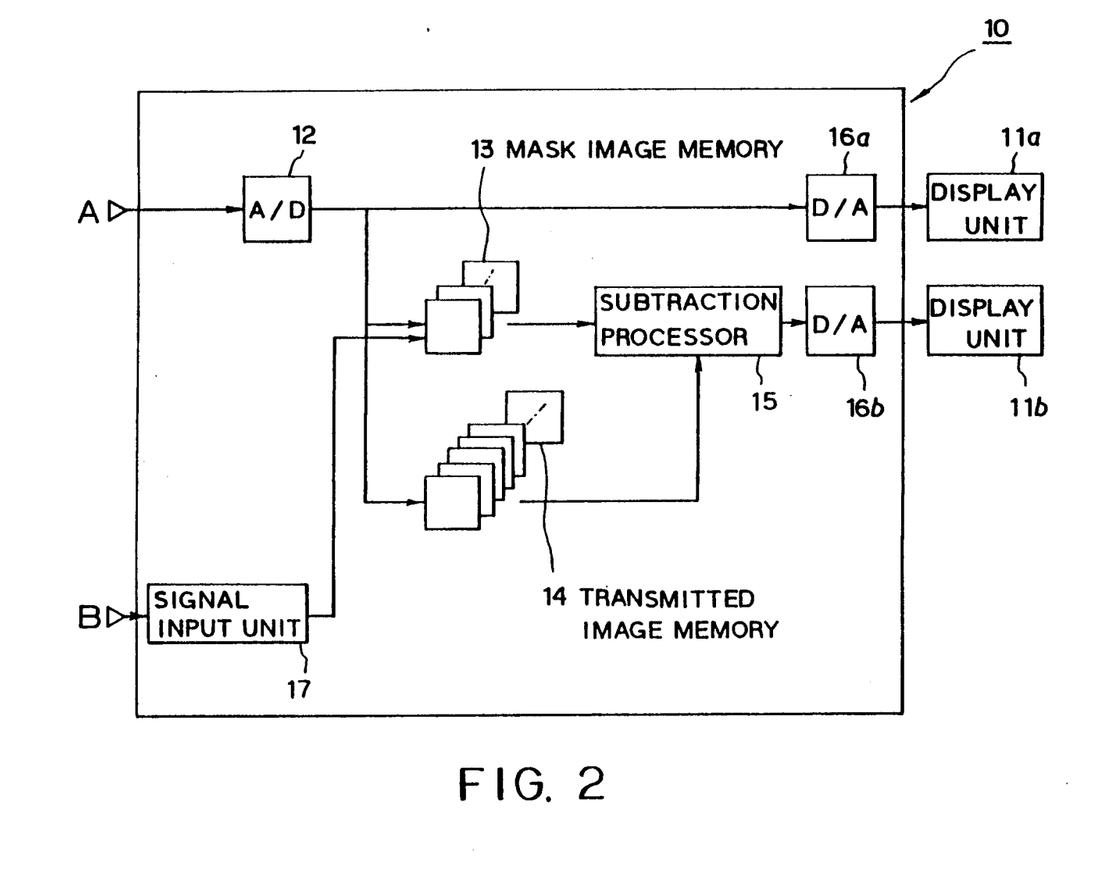
FIG. 2 is a block diagram showing a construction of DF device in the apparatus of FIG. 1.

FIG. 2 is a block diagram showing a detailed construction of the DF device 10, which includes an A/D (analog-to-digital) converter 12 for converting the signal A into a digital signal, a mask image recording picture memory 13 for recording digital video signals immediately before injecting a contrast medium successively as a mask image, a transmitted image recording picture memory 14 for recording the digital video signals after injecting the contrast medium successively as a transmitted image, a subtraction processor 15 for subtracting the transmitted image from the mask image, D/A converters 16a and 16b for converting the digital video signal into an analog video signal, a signal input unit 17 for inputting the signal B indicating that the imaging conditions outputted by the controlling unit 9 are decided.

The video signal A outputted from the TV camera 5 is once converted into a digital signal by the A/D converter 12, and reconverted into an analog signal by the D/A converter 16a, and displayed on the TV monitor 11a as a transmitted image. Then, the video signal A is sent to the mask image recording picture memory 13 and the transmitted image recording picture memory 14. The digital video signal just before the imaging process is commenced and a contrast medium injected is recorded in the picture memory 13 as a mask image. The contrast medium is then injected, and a picture image with a portion to be diagnosed of the subject drawn by the contrast medium is recorded in the picture memory 14 as a transmitted image. Then, these mask image and transmitted image are read concurrently out of the picture memories 13 and 14 respectively, and after the transmitted image is subtracted from the mask image by the subtraction processor 15, the image is converted again into an analog signal by the D/A converter 16b and displayed on the TV monitor 11b as DSA image.

In case the imaging system is moved during the imaging process, the imaging conditions are subjected to an automatic control. When the signal B indicating that the imaging conditions are decided is inputted after the imaging system is stopped moving, video signals inputted to the A/D converter 12 are recorded successively as a second mask image in an area different from the area in which the mask image (first mask image) of the picture memory is recorded. The second mask image and the transmitted image are read concurrently out of the picture memories 13 and 14 respectively thereafter, and after the transmitted image is subtracted from the second mask image by the subtraction processor 15, the image is displayed on the TV monitor 11b as a DSA image to the second mask image.

Similarly, in case the imaging system moves again, when the signal B indicating that the imaging conditions are decided after the stop of the movement is inputted, a third mask image is recorded in the picture memory, the transmitted image is subtracted from the third mask image, and a DSA image to the third mask image is displayed on the TV monitor 11b. DSA images to those of a fourth mask image and so on may be displayed accordingly thereto.

Figure 3:
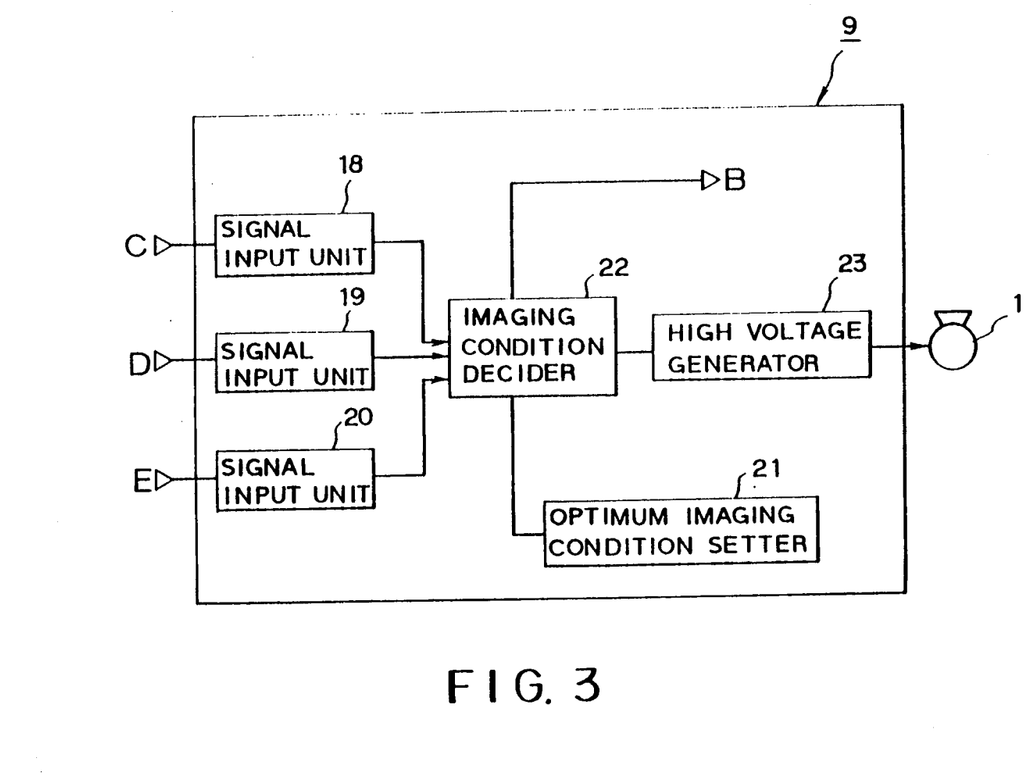
FIG. 3 is a block diagram showing a construction of a controlling unit in the apparatus of FIG. 1.

FIG. 3 is a block diagram showing a detailed construction of the controlling unit 9, which includes a signal input unit 18 for inputting an electrical signal transformed from an optical signal by the photoelectron multiplier 6 as the signal C indicating an outgoing light of the I. I., a signal input unit 19 for inputting the signal D indicating that the imaging system moves from the imaging system support 7 and a signal input unit 20 for inputting the signal E indicating that the subject 2 moves from the bed 8. The controlling unit 9 further includes an imaging condition setter 21, an optimum imaging condition decider 22 and a high voltage generator 23.

X-rays having passed through the subject 2 laid on the bed 8 are transformed into an optical signal by the I. I. 3 and incident on the TV camera 5 through the optical system 4, and a part of the optical signal is transformed into an electrical signal by the photoelectron multiplier 6 in the optical system 4 and is inputted through the signal input unit 18. The input electrical signal is then inputted to the imaging condition setter 21 together with a reference value signal corresponding to an optical signal at the time of the optimum imaging conditions set beforehand by the optimum imaging condition decider 22. The optical information actually detected and the optimum value are compared by the imaging condition decider 22.

In case the comparison result comes outside a tolerance, a signal for adjusting the imaging conditions is inputted to the high voltage generator 23, thereby optimizing the imaging conditions. On the other hand, if the comparison result comes within the tolerance, then the signal B indicating that the imaging conditions are decided is outputted to the DF device 10.

Here, a control of the imaging conditions is made to function before the start of the imaging process and once the imaging conditions are decided, the imaging conditions are fixed as decided and not changed after the start of the imaging process regardless of a change in actual optical information from a contrast medium being injected therefor.

However, when the signal D indicating a movement of the imaging system or the signal E indicating a movement of the subject is inputted to the signal input unit 19 or 20, the imaging conditions will be decided from comparing the actual optical information with the optimum value. The imaging conditions function continuously while both the signals D and E are inputted. After the imaging system is stopped moving and the subject is also stopped moving, the actual optical information is compared with the optimum value, and when coming outside a tolerance, a decision function of the imaging conditions is continued further, but when coming within the tolerance, the decision function is closed, the imaging conditions are thus fixed, and the signal B indicating a decision of the imaging conditions is outputted.

An operation of the embodiment will be described with reference to flowcharts of FIGS. 4 and 5.

Figure 4:
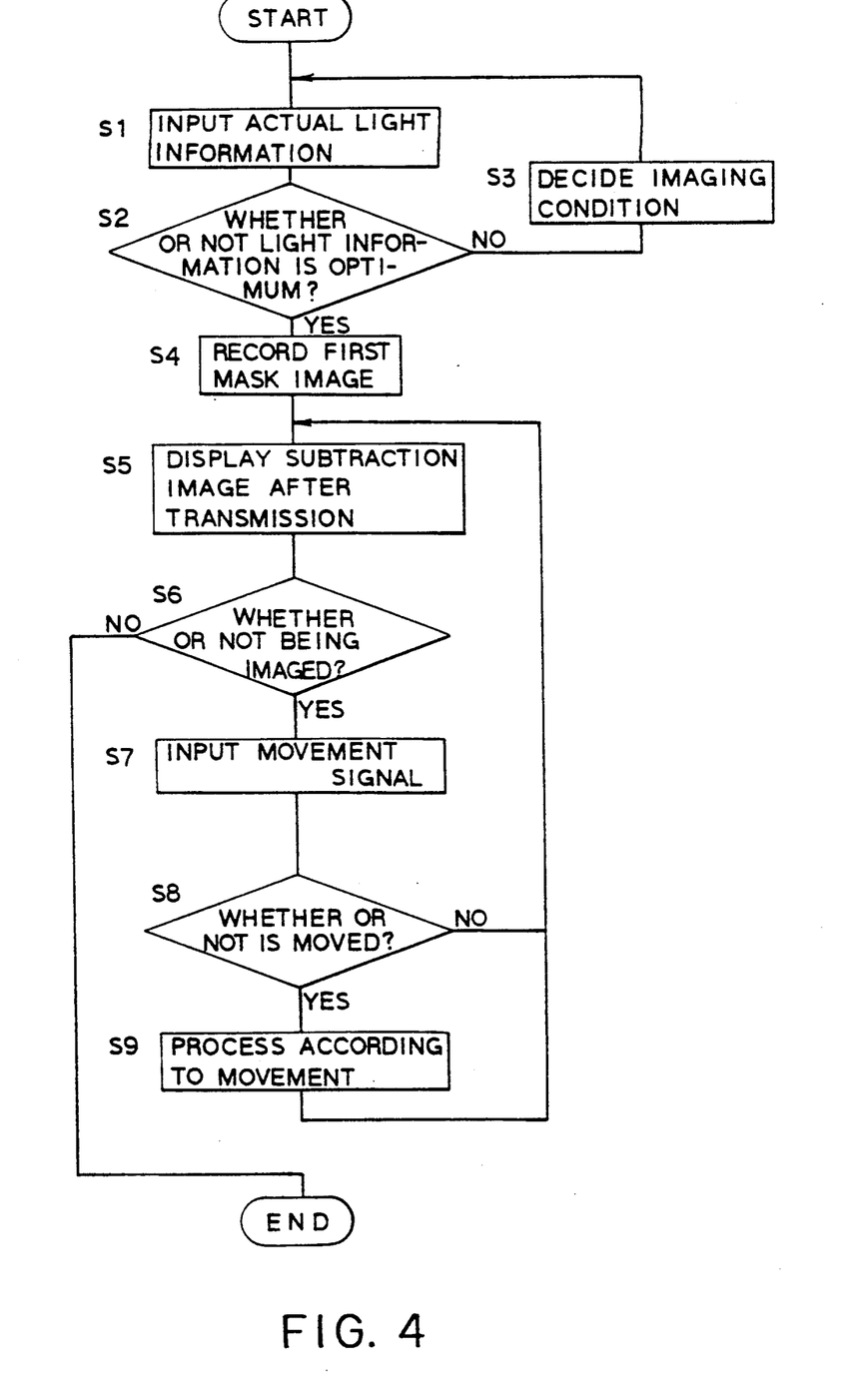
FIG. 4 and FIG. 5 are flowcharts for explaining an operation the embodiment.

FIG. 4 is a general flowchart indicating a procedure for X-ray imaging process, wherein an actual optical information is detected first in step S1 by the photoelectron multiplier 6. Next in step S2, the optical information and an optimum value are compared with each other by the imaging condition decider 22, thereby deciding whether or not the optical information is optimum. If not optimum, then the flow proceeds to step S3, where the imaging conditions are decided to return to step S1, and thus the operation is repeated until a comparison result is optimized.

When the comparison result is optimum, the flow proceeds to step S4, where the first mask image is recorded in the picture memory 13. Next the first mask image and the transmitted image are subjected to a subtraction process, the transmitted image is displayed on the TV monitor 11a in step S5, and a DSA image (subtraction image) is displayed on the TV monitor 11b likewise. Next, whether or not an imaging process is going is decided in step S6. If not, then it is nothing to do with the embodiment, and hence the flow comes to an end. If the imaging process is going, the flow proceeds to step S7, where the signal D indicating that the imaging system moves or the signal E indicating that the subject 2 moves is inputted to the controlling unit 9.

Whether or not moved is decided in step S8, and if not, then the flow returns to step S5. When not moved, the transmitted image and the DSA image are displayed repeatedly on each TV monitor with the imaging conditions fixed. When moved, the flow proceeds to step S9, where a process according to the movement is carried out as shown in FIG. 5. When moved, the imaging conditions are controlled and optimized within a given period of time during movement and after stop of the movement.

Figure 5:
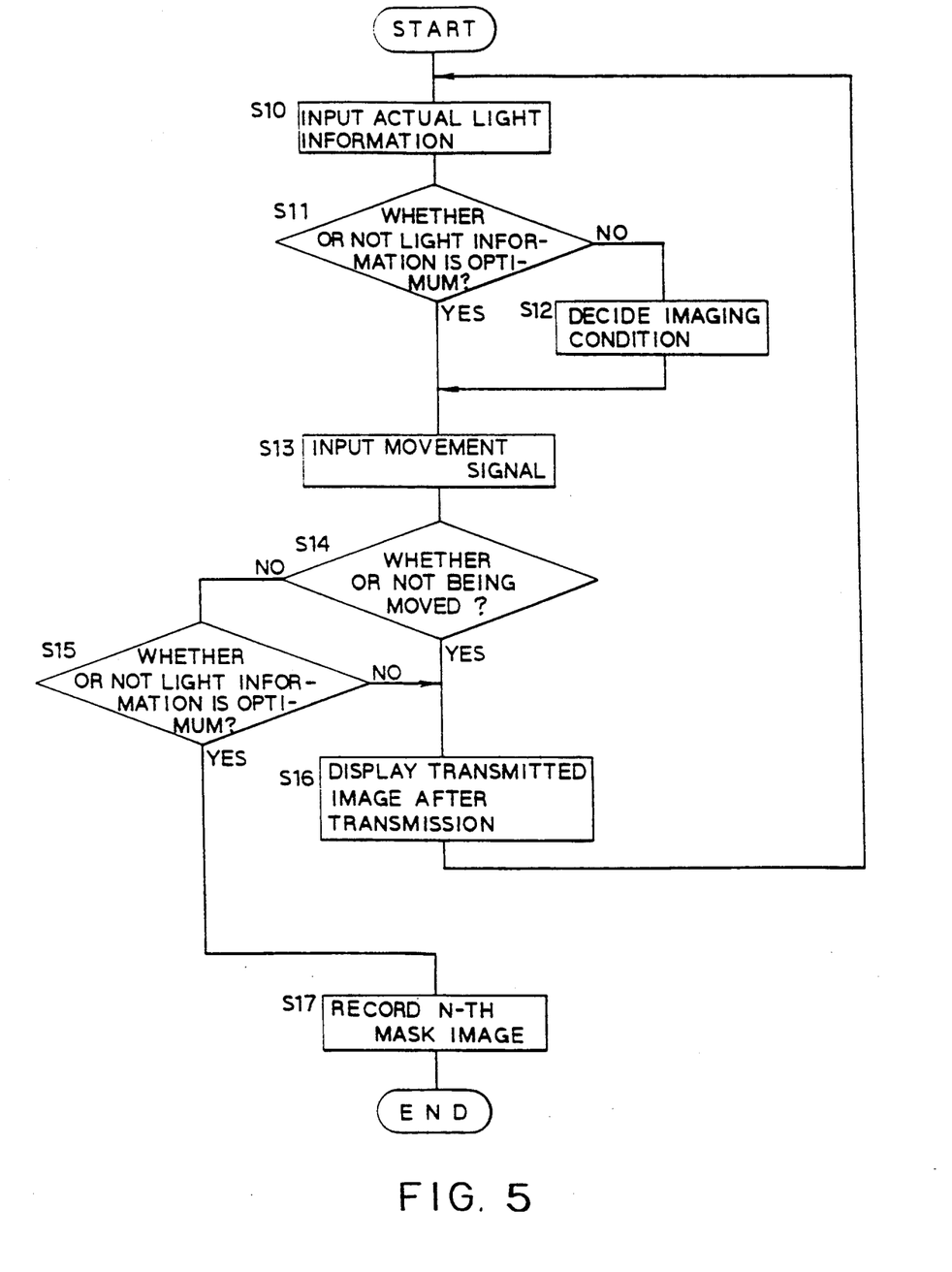

Referring to FIG. 5, an actual optical information is inputted first by the photoelectron multiplier 6 in step S10. Next in step S11, the optical information and the optimum value are compared by the imaging condition decider 22, thereby deciding whether or not the optical information is optimum. When not optimum, the flow proceeds to step S12, where imaging conditions are decided, and then the flow proceeds to step S13. Where the comparison result is optimum, the flow proceeds to step S13 without passing the step S12.

In step S13 the signal D indicating that the imaging system moves or the signal E indicating that the subject moves is inputted to the controlling unit 9.

In step S14, whether or not moving is decided, and if not, the flow proceeds to step S15, but if moving, the flow proceeds to step S16. In the step S16, a mask image and a transmitted image are subjected to a subtraction process, the transmitted image is displayed on the TV monitor 11a and a DSA image is displayed on the TV monitor 11b. The flow then returns to step S10 and a similar operation is repeated.

If the movement comes to stop, whether or not an actual optical information is optimum is decided through a comparison with the optimum value, and when not optimum, the flow proceeds to step S16. Where it is optimum, the defined signal B of imaging conditions is outputted, thus the transmitted image is recorded as the second mask image, and where the flow is repeated, the n-th mask image is recorded in step S17.

Figure 6:
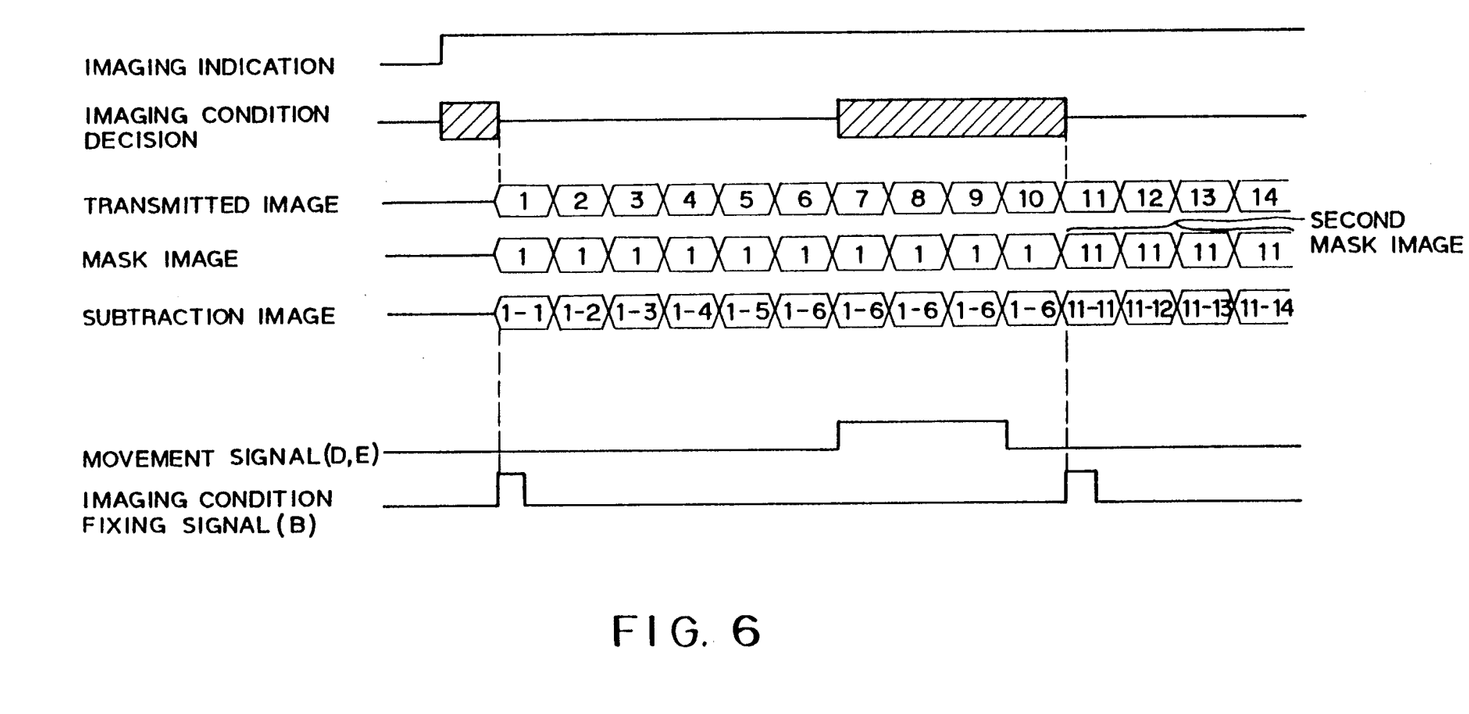
FIG. 6 is a timing chart for illustrating the operation of the embodiment.

FIG. 6 indicates a time-chart indicating the above described operation of the diagnosis apparatus of the present embodiment. The mask image is recorded whenever the imaging condition defined signal B is outputted, and the second mask image, the third mask image and so on can be obtained in each occasion.

As described above, according to this embodiment, the imaging conditions are fixed while the imaging system and the subject are fixed, and the imaging conditions are stopped for a given period of time while the imaging system and the subject are moving and after the movement is stopped, therefore a picture imaged when the imaging system or the subject is fixed can be applied effectively to an arithmetic operation. Further, the imaging system and the subject are moved, the optimum X-ray imaging conditions can be set according to a change of the subject, therefore a density of the contrast image can be optimized and the DSA image free from change in density is obtainable. In addition, the DSA image not shifted at a position after the imaging system or the subject is moved is obtainable. Thus in addition to a diagnosis according to an observation of the contrast image, the DSA image after movement of the imaging system or the subject can be obtained. In case, further, where a volume of contrast medium flows into the contrast image, since a density of the ambient tissue of the subject, i.e. patient, does not change, a picture easy to see is obtainable.

While in the foregoing descriptions there has been taken, for describing the preferred embodiment, a case wherein an optical information is detected by the photoelectron multiplier, a similar effect will be obtained from detecting the optical information by taking advantage of a video signal outputted from the TV camera. Further, in the embodiment, a subtraction process is continued for a given period of time while the imaging system or subject moves and after these stop moving, however, an effect will be ensured such that an artifact image during fluctuation of the imaging conditions will not be displayed by interrupting the subtraction process to display nothing or by displaying the DSA image just before start of the movement.

As described above, according to the present invention a density of the contrast image while the imaging system is fixed can be optimized and the DSA image free from change in density can be provided, In addition, the DSA image not shifted at a position after movement of the imaging system can be provided, thus a diagnostic efficiency being enhanced.

It is to be understood that the present invention is not limited to the described preferred embodiment and other changes and modifications may be made within the scope of the appended claims.

What is claimed is

1. An X-ray diagnostic apparatus including an imaging system in which X-rays are applied to a subject and a picture image in response to an X-ray dose transmitted through the subject is displayed, comprising:

an X-ray generator for generating an X-ray;

means for detecting the X-ray generated from the X-ray generator and passing through the subject disposed between the X-ray generator and the detecting means and for generating a signal in response to the detected X-ray;

means operatively connected to the detecting means for deciding an optimum imaging condition for a portion of the subject to be imaged before a start of an imaging process;

means for detecting whether the imaging system or the subject is being moved or not;

for controlling the imaging condition within a predetermined interval of time during or after the movement of the imaging sytem or the subject; and display means connected to the optimum condition deciding means.

2. The apparatus according to claim 1, wherein said imaging condition deciding means includes signal input means including signal input units for inputting siganls from the X-ray detecting means and the imaging system and subject movement detecting means, an optimum imaging condition setter operatively connected to the signal input means and an imaging condition decider and wherein said controlling means includes a high voltage generator operatively connected to the optimum imaging condition setter and the X-ray generator.

3. The apparatus according to claim 1, wherein said means for detecting the movement of the imaging system or the subject comprises a digital fluorography device including an analog-to-digital converter for converting a signal from the X-ray detecting means to a digital signal, a signal input unit operatively connected to the controlling means, a first recording memory for recording the digital signal just before injecting a contrast medium successively as a mask image, a second recording memory for recording the digital signal after injecting the contrast medium succesively as a transmitted image, and a subtraction processor for subtracing the transmitted image from the mask image.

4. The apparatus according to claim 3, wherein said subtraction processor is operatively connected to the display means through a digital-to-analog convertor.

* * * * *